United States Patent [19]

Ams et al.

[11] Patent Number: 4,995,877
[45] Date of Patent: Feb. 26, 1991

[54] DEVICE WITH A ROTATIONALLY-DRIVEN SURGICAL INSTRUMENT

[75] Inventors: Felix Ams, Kämpfelbach; Manfred Baier, Bretten; Roland Schäfer, Bretten-Diedelsheim, all of Fed. Rep. of Germany

[73] Assignee: Richard Wolf GmbH, Fed. Rep. of Germany

[21] Appl. No.: 311,758

[22] Filed: Feb. 17, 1989

[30] Foreign Application Priority Data

Feb. 19, 1988 [DE] Fed. Rep. of Germany ....... 3805179

[51] Int. Cl.$^5$ .............................................. A61B 17/32
[52] U.S. Cl. .................... 606/180; 606/80; 606/167
[58] Field of Search ............... 606/167, 168, 170, 171, 606/180, 79, 80, 81, 84; 604/22; 433/98, 99; 30/500

[56] References Cited

U.S. PATENT DOCUMENTS

| | | |
|---|---|---|
| 3,732,858 | 5/1973 | Banko . |
| 4,203,444 | 5/1980 | Bonnell et al. ...................... 128/276 |
| 4,274,414 | 6/1981 | Johnson et al. ...................... 128/305 |
| 4,705,038 | 10/1987 | Sjostrom et al. ...................... 128/305 |

OTHER PUBLICATIONS

Sales for Concept Incorporated.

*Primary Examiner*—Michael H. Thaler
*Attorney, Agent, or Firm*—Hill, Van Santen, Steadman & Simpson

[57] ABSTRACT

The device comprises a rotationally driven surgical instrument incorporating a hand-held element having a mount rotatably installed therein for reception of interchangeable cutting and milling inserts, a driving motor for driving the mount receiving the tool inserts, a control unit for controlling the driving motor with means of setting the rotational speed and of preselecting the rotational speed range and direction of rotation as well as a digital indicator for displaying the rotational speed set up in each case. For the purpose of accessible storage of setting data, the control unit incorporates a nonvolatile read-write memory for digital storage of rotational speeds, a code carrier as well as a coding/decoding arrangement.

8 Claims, 1 Drawing Sheet

DEVICE WITH A ROTATIONALLY-DRIVEN SURGICAL INSTRUMENT

BACKGROUND OF THE INVENTION

The invention relates to a device comprising a rotationally driven surgical instrument having a hand-held element provided with a mount rotatably installed therein for reception of interchangeable cutting and milling inserts, a driving motor for driving the mount receiving the tool inserts, a control unit for controlling the driving motor with means of setting the rotational speed and of preselecting the rotational speed range and direction of rotation, as well as a digital indicator for display of the rotational speed set in each case.

DESCRIPTION OF THE PRIOR ART

In German Patent Specification No. 2,848,314 a surgical instrument is disclosed for arthroscopic intra-articular joint surgery which, without having to perform a joint opening operation, renders it possible for example to pare down synovial tissue, to perform a partial meniscus surgical removal, to treat cartilage defects or the like, by means of an endoscopic operation. The rotational speed of the cutting or milling inserts revolving in an external shaft may be adjusted at the driving motor coupled to the instrument via a flexible shaft, within the range from 100 to 200 revolutions per minute. The possibility exists moreover of removing the cut tissue, cartilage or bone parts through the hollow cutter or miller insert by means of a vacuum line connectable to the instrument.

In European Patent Application No. 0,189,807 a surgical instrument is also disclosed comprising a plurality of adaptors which are situated between the motor handle and the cutting insert and set the rotational speed of the cutting or milling insert in use at that time. Since the different cutting inserts have to be operated at different rotational speeds, this requires that an adaptor be allocated for each of the inserts.

Finally, a surgical instrument for arthroscopic treatment of joints is known, which is sold by the Concept Company under the name INTRA-DRIVE SYSTEM. Although the incorporation of a plurality of sensors present at the distal extremity of the handle may well allow the instrument to be turned on and off, to change the direction of rotation as well as to set the rotational speed within two rotational speed ranges, the prior art carries the disadvantage that the rotational speed which is an optimum in the opinion of the current user has to be reset during every utilization of the instrument and at each replacement of the cutting insert, because instruments of this nature are commonly available to several users, who select different rotational speeds as a function of the surgical operation which is to be performed, of the cutting insert utilized and of experience. The time required to establish the optimum rotational speed as well as the determination of the optimum rotational speed itself, represent an unacceptable nuisance to the surgeon as well as to the patient.

SUMMARY OF THE INVENTION

It is accordingly an object to provide a device comprising a control unit for driving a surgical instrument of the type referred to in the foregoing, which is adapted to store individual setting data in an accessible manner.

This object is achieved by the device, in accordance with the invention, in that the control unit comprises a non-volatile write-read memory for digital storage of user-specific rotational speeds and the like, a code carrier as well as a coding/decoding arrangement. In this connection, a preferred form of embodiment consists in that the code carrier may be coupled releasably to the control unit, which is advantageously authorized by the fact that the code carrier is constructed as a card, key, plug, or the like.

Setting data which had previously been found and checked as being advantageous may consequently be stored in their entirety and transferred to a code carrier which performs an individual setting action at any time upon being placed in communication with the decoding arrangement.

For the purpose of activating and deactivating the control unit, the latter may have associated with it a switching arrangement adapted to be foot-operated, for turning the driving motor on and off and for changing its direction of rotation. The switching arrangement may however also be allocated to the hand-held element for turning the driving motor on and off and for changing its direction of rotation, for this purpose. The different cutting and milling inserts utilized should be operated within specific rotational speed ranges to develop their efficiency. By means of a coding of the cutting and milling inserts corresponding to the rotational speed range required in each case, it is possible to obtain an automatic rotational speed range preselection specific to the tool, thanks to the fact that the hand-held element comprises an arrangement for conversion of the code allocated to the cutting and milling inserts into an electrical signal which is evaluated by the control unit. To this end, the coding method may be of electrical, optical or magnetic type, so that the decoding arrangement in the hand-held element should be constructed accordingly.

To secure a more effective cutting performance, the control unit may be so devised as a function of the cutting tool utilized, that it authorizes a method of operation wherein the direction of rotation of the driving motor changes periodically, the change-over occurring for example after completion of at least one complete revolution in each case. Another simplification of the means of operating the instrument according to the invention may be accomplished if the control unit incorporates a voice input arrangement which authorizes a voice-operated functional control. Finally, the control unit may comprise connecting means for the purpose of documentation, by means of which the data set up may be transferred into an external recording apparatus and/or may be gated into an endoscope image on a monitor, for example.

BRIEF DESCRIPTION OF THE DRAWINGS

The device according to the invention is described in particular in the following, with reference to a preferred embodiment illustrated in the drawings. In these.

DETAILED DESCRIPTION OF THE PREFERRED EMBODIMENT

Figure 1:
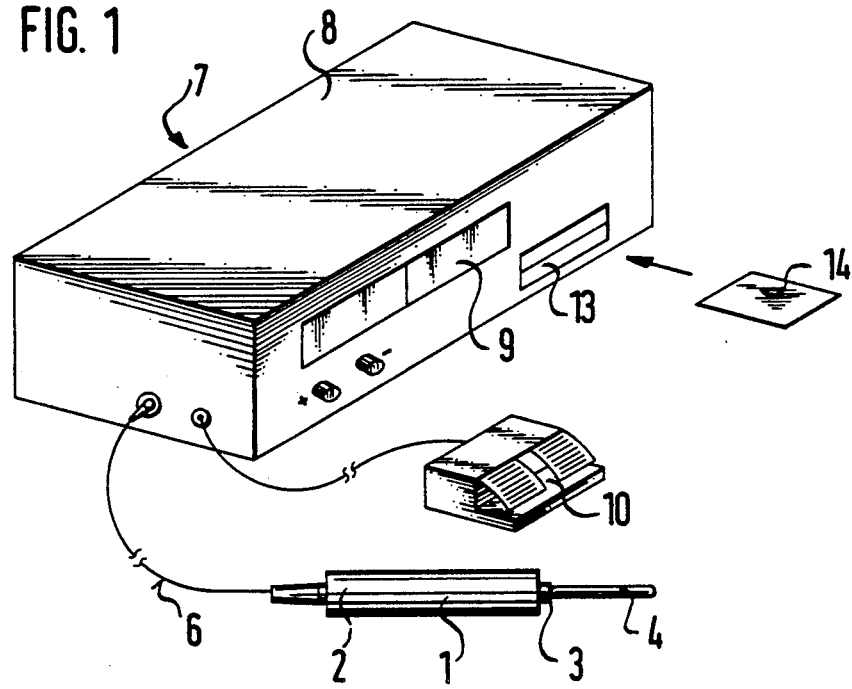
FIG. 1 shows a schematic view of the complete device.
Figure 2:
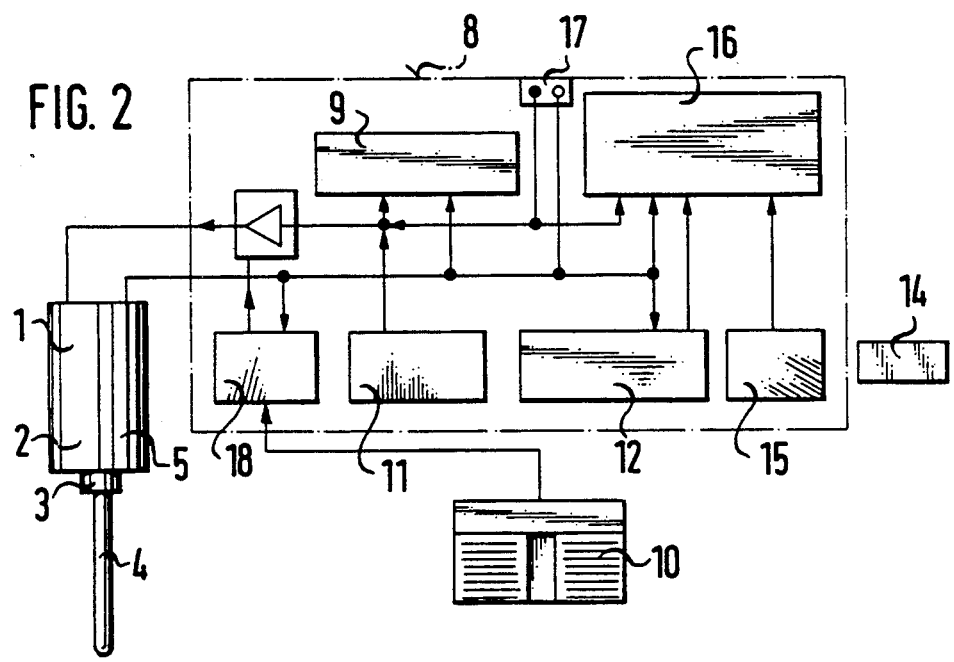
FIG. 2 shows the device in a schematic illustration as a block circuit diagram.

As is apparent from the drawings, the hand-held element 1 comprises a driving motor 2 driving a mount 3 receiving the cutting and milling inserts 4, as well as a decoder 5 for conversion of the code allocated to the cutting and milling inserts 4 in each case, into corresponding electrical signals. The hand-held element 1 is connected via a lead 6 to a control unit 7 which is installed in an appropriate housing 8. Externally visible elements of this control unit 7 are a display 9 for indication of the rotational speed set up and of the kind of tool being utilized and, a connector for a foot-switch 10 devised for the purpose of activation and deactivation as well as for reversing the direction of rotation of the driving motor 2. The housing 8 (FIG. 2) contains a control arrangement 11 for setting the rotational speed, a rotational speed range selector 12 as well as a plug-in facility 13 (FIG. 1) for a code carrier 14. The plug-in facility 13 is connected to a coder/decoder 15 (FIG. 2) which for its part corresponds with a storage unit 16.

In preparation for the operation of the device according to the invention, the current user performs a manual setting of the operational data such as the rotational speed, its initial and final values, etc. and optimizes these in accordance with his own judgement. The operational data established in this manner are stored in the storage unit 16 which comprises a corresponding number of storage locations for this purpose. The contents of these storage locations may be transferred to a code carrier 14, for example in the form of a magnetic card, by inserting the latter into the plug-in facility 13 provided for this purpose. The owner of this code carrier is thus able conversely to call up the preprogrammed data by insertion of the magnetic card, that is to say to adjust the control unit 7 to the corresponding data by this action. In this connection and in the case of the utilization of tool inserts coded in the manner referred to above, it is possible to preset a rotational speed range, a readjusting operation being able to be performed between its top and bottom rotational speed limits. Each user may make use of an individual code carrier in this manner, by means of which the device may at any time be set to the data established in an empirical manner for example and considered to be of optimum nature, simply by inserting the carrier into the plug-in facility 13. The device adjusted in this manner may then be activated or deactivated via the control 18 of the direction of rotation, by operating the foot-switch 10 whilst the direction of rotation may also be set via the same.

The setting data may be transferred via an appropriate connection 17 to an external recording apparatus whereby it is possible to record the course of the operation, for example for teaching purposes or for the purpose of documentation. The operation may however also be followed externally by connection of a monitor which for example reproduces the endoscopic image of the operating area, into which the setting data are gated in.

In conclusion, it is also pointed out that no more than the user's person-related code may be marked on the code carrier in question, whereas the data which are to be stored such as the rotational speed, direction of rotation, rotational speed ranges and the like are stored in the internal system memory and may be called up via the code carrier. On the other hand, the data which are to be stored and those relating to the user may also be stored direct on the code carrier, so that these data are scanned upon inserting the code carrier into the device and transferred to the internal system memory. In this case, a separate person-related code is furthermore unnecessary.

What is claimed is:

1. A device comprising:
    a rotationally driven surgical instrument having a hand-held element;
    interchangeable cutting and milling inserts;
    a mount rotatably installed in said hand-held element for reception of said interchangeable cutting and milling inserts;
    a driving motor for driving the mount receiving the cutting and milling inserts, and;
    a control unit for controlling the driving motor including means for setting a rotational speed of the motor and for preselecting a rotational speed range and also an indicator for display of the rotational speed set in each case; said control unit comprising a non-volatile write-read memory for digital storage of user-specific rotational speed data,
    a code carrier remote from said cutting and milling inserts and removable from said control unit, said code carrier carrying a reprogrammable encoding corresponding to speed data in said write-read memory, said encoding on said code carrier being reprogrammable by a user to set said surgical instrument to a user selected rotational speed range, and also
    a means for coding/decoding said encoding on said code carrier, said means for coding/decoding selectively receiving said code carrier for reading said encoding.

2. A device according to claim 1, wherein the code carrier is constructed as a card, key, or plug.

3. A device according to claim 1, wherein the control unit has allocated to it a switching arrangement adapted to be foot-operated for turning the driving motor on and off and for changing its direction of rotation.

4. A device according to claim 3, wherein the switching arrangement for turning the driving motor on and off and for changing its direction of rotation is associated with the hand-held element.

5. A device according to claim 1, wherein the hand-held element incorporates a further decoder for conversion of a further code allocated to the cutting and milling inserts into an electrical signal which is evaluated by the control unit.

6. A device, according to claim 1, wherein the control unit includes means for allowing a method of operation to be applied as a function of the cutting tool, in which the direction of rotation of the driving motor changes periodically, the change-over occurring in each case after completion of at least one complete revolution.

7. A device according to claim 1, wherein the control means comprises connecting means whereby the data set up can be transmitted to an external recording apparatus and/or gated into an endoscope image on a monitor.

8. A device according to claim 1, wherein the control unit has a switching arrangement in the hand-held element for turning the drive motor on and off and for changing the direction of rotation of the drive motor.

* * * * *